United States Patent [19]

Krishnan et al.

[11] Patent Number: 4,578,409
[45] Date of Patent: Mar. 25, 1986

[54] FLAME RETARDING SILANES

[75] Inventors: Sivaram Krishnan, Pittsburgh, Pa.; Ulrich R. Grigo, Kempen, Fed. Rep. of Germany; Donald A. Folajtar, Pittsburgh, Pa.

[73] Assignee: Mobay Chemical Corporation, Pittsburgh, Pa.

[21] Appl. No.: 691,102

[22] Filed: Jan. 14, 1985

[51] Int. Cl.$^4$ .............................................. C08K 5/34
[52] U.S. Cl. ........................................ 524/94; 524/165; 524/394; 524/406; 524/408; 524/409; 524/411; 524/413; 524/415; 524/436; 524/437; 524/493; 524/539; 524/590; 524/546; 548/406
[58] Field of Search ............... 524/94, 165, 539, 540, 524/546, 394, 437; 548/406

[56] References Cited

U.S. PATENT DOCUMENTS

| | | | |
|---|---|---|---|
| 2,487,105 | 11/1949 | Cornwell | 524/94 |
| 3,775,367 | 11/1973 | Nouverné | 524/165 |
| 3,868,388 | 2/1975 | Dotson et al. | 260/326 |
| 3,873,567 | 3/1975 | Cyba | 260/326 |
| 3,901,913 | 8/1975 | Kim | 548/406 |
| 3,915,930 | 10/1975 | Dotson et al. | 260/45.8 |
| 3,919,167 | 11/1975 | Mark | 260/45.8 |
| 3,923,734 | 12/1975 | Dotson et al. | 260/45.75 |
| 3,933,734 | 1/1976 | Mark | 260/45.7 |
| 3,940,366 | 2/1976 | Mark | 260/45.9 |
| 3,971,756 | 7/1976 | Bialous et al. | 260/45.7 |
| 4,001,179 | 1/1977 | Richter et al. | 260/45.75 |
| 4,003,862 | 1/1977 | Albright | 260/2.5 |
| 4,066,618 | 1/1978 | Mark | 260/45.85 |
| 4,067,846 | 1/1978 | Mark | 260/45.9 |
| 4,069,201 | 1/1978 | Mark | 260/45.95 |
| 4,073,678 | 2/1978 | Hammond et al. | 162/19 |
| 4,075,164 | 2/1978 | Mark | 260/45.7 |
| 4,087,441 | 5/1978 | Lee | 260/326 |
| 4,093,589 | 6/1978 | Factor | 260/45.75 |
| 4,223,100 | 9/1980 | Reinert | 524/409 |
| 4,320,049 | 3/1982 | Krishnan et al. | 524/94 |
| 4,414,396 | 11/1983 | Boyer | 524/94 |

FOREIGN PATENT DOCUMENTS 1287934 9/1972 United Kingdom .
2030983 4/1980 United Kingdom ............... 548/406

Primary Examiner—John Kight
Assistant Examiner—Kriellion Morgan
Attorney, Agent, or Firm—Gene Harsh; Lawrence S. Pope; Aron Preis

[57] ABSTRACT

The present invention relates to a novel halogenated silane conforming to the structure

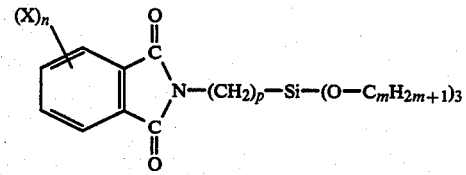

where X is a halogen atom, n is an integer of from 1 to 4, p is an integer of from 1 to 9 and m is an integer of from 1 to 5. The silane thus disclosed was found to be particularly suitable as a flame retarding additive for thermoplastic molding compositions.

11 Claims, No Drawings

FLAME RETARDING SILANES

FIELD OF THE INVENTION

The invention relates to flame retarding compounds suitable in improving the flammability rating of thermoplastic molding compositions and more particularly to halogenated phthalimide silanes.

SUMMARY OF THE INVENTION

The presently disclosed novel silane which conforms structurally to

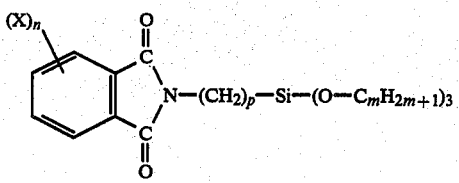

wherein X is a halogen, preferably chlorine or bromine, n is 1 to 4, p is 1 to 9, preferably 2 to 4, m is 1 to 5, preferably 1 to 3, is an effective flame retarding agent suitable in improving the flammability rating of thermoplastic molding compositions, preferably ones comprising polycarbonates or aromatic polyesters. Among the characteristics making the silane of the present invention particularly suitable in compositions comprising polycarbonate, or polyester resins is its low degree of volatility.

BACKGROUND OF THE INVENTION

Flame retarding additives for use in polymeric compositions include phosphates, phosphoric acid esters and thio-phosphoric acid esters containing halogenated alkyl radicals. Also, metal salts notably sulfonate salts of alkali or alkaline earth metals have been disclosed to improve the flame retardance of polycarbonates. Further, chlorine or bromine substitutions in some of the phenolic diols used in the preparation of polycarbonates have been disclosed to impart flame retardance to the polycarbonate resin.

Illustrative of the sulfonic acid salts and of metal salts are those disclosed in U.S. Pat. Nos. 3,775,367; 4,067,846; 4,073,678; 4,075,164; 4,066,618; 4,069,201; 4,093,589; 3,971,756; 3,933,734; 3,940,366, and 3,919,167.

Some of these flame retardants, however, in order to be effective, are added in relatively large amounts such as to adversely effect some of the desirable properties of the base resin. For example, both the impact strength and the hydrolytic stability are compromised upon addition of large quantities of salt. Further, many of these flame retarding salts are susceptible to volatilizaton at the high molding temperatures of polycarbonates, necessitating thus the addition of excess amounts of salt which in turn bring about haze and loss of transparency. Since there is no uniformity of processing conditions among molders, it becomes difficult, if not impossible, to regulate the ultimate amount of salt incorporated into the resins.

Flame retardants incorporating a phthalimide group have been disclosed in, for instance, British Pat. No. 1,287,934 and U.S. Pat. Nos. 3,873,567; 3,923,734; 3,915,930; 3,868,388; 4,087,441; 4,001,179; 4,003,862 and 4,320,049.

DETAILED DESCRIPTION OF THE INVENTION

The preparation of the novel compounds of the invention may be carried out by reacting a halogenated phthalic anhydride with an aminoalkyl trialkoxy silane. Examples 1 and 2 are demonstrative of the procedure.

The flame retarding agents of the invention are useful in improving the flame resistance of thermoplastic molding compositions and the articles formed therefrom. In the present context, the preferred thermoplastic molding compositions include the ones comprising polycarbonates or thermoplastic polyesters for instance poly(alkylene)terephthalate.

The polycarbonate resins useful in the practice of the invention are homopolycarbonate, copolycarbonate and terpolycarbonate resins or mixtures thereof. The polycarbonate resins generally have molecular weights of 10,000-200,000 (weight average molecular weight) preferably 20,000-80,000, and may alternatively be characterized by their melt flow of 1-24 gm/10 min. at 300° C. per ASTM D-1238. These polycarbonates may be prepared, for example, by the known diphasic interface process from phosgene and dihydroxy compounds by polycondensation (see German OS Nos. 2,063,050; 2,053,052; 1,570,703; 2,211,956; 2,211,957 and 2,248,817 and French Pat. No. 1,561,518 and the monograph, H. Schnell, *Chemistry and Physics of Polycarbonates,* Interscience Publishers, New York, 1964, all incorporated herein by reference).

In the present context, dihydroxy compounds suitable for the preparation of the polycarbonates of the invention conform to the structural formulae (1) or (2)

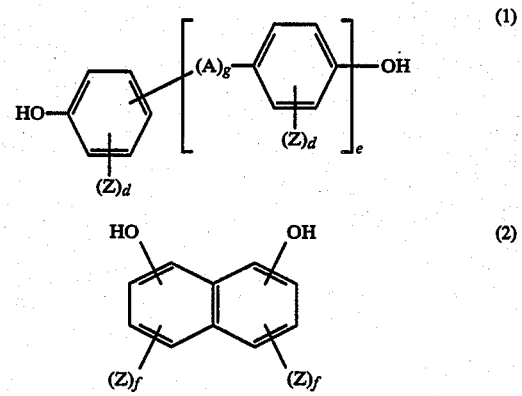

wherein

A denotes an alkylene group with 1 to 8 carbon atoms, an alkylidene group with 2 to 8 carbon atoms, a cycloalkylene group with 5 to 15 carbon atoms, a cycloalkylidene group with 5 to 15 carbon atoms, a carbonyl group, an oxygen atom, a sulfur atom, an —SO— or —SO$_2$— radical; a radical of the general formula

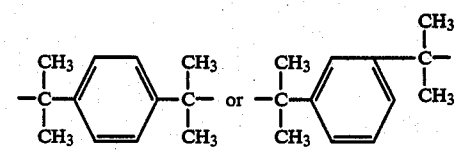

g denotes the number 0 or 1;

e denotes the number 0 or 1;

Z denotes F, Cl, Br or a $C_1$–$C_2$ alkyl and if several Z radicals are substituents in one aryl radical, they may be identical or different;

d denotes 0 or an integer of from 1 to 4; and f denotes 0 or an integer of from 1 to 3.

Among the useful dihydroxy compounds in the practice of the invention are hydroquinone, resorcinol, bis-(hydroxyphenyl)-alkanes, bis-(hydroxyphenyl)-cycloalkanes, bis-(hydroxyphenyl)-ethers, bis-(hydroxyphenyl)-ketones, bis-(hydroxyphenyl)-sulfoxides, bis-(hydroxyphenyl)-sulfones and α, α-bis-(hydroxyphenyl)-diisopropyl-benzenes. These and further suitable aromatic dihydroxy compounds are described, for example, in U.S. Pat. Nos. 3,028,365; 2,999,835; 3,148,172; 3,271,368; 2,991,273; 3,271,367; 3,280,078; 3,014,891 and 2,999,846 (all incorporated herein by reference), in German Offenlegungsschriften (German Published Specifications) Nos. 1,570,703; 2,063,050; 2,063,052; 2,211,956 and 2,211,957, in French Patent Specification No. 1,561,418 and in the monograph, H. Schnell, *Chemistry and Physics of Polycarbonates,* Interscience Publishers, New York, 1964. Further examples of suitable dihydroxy compounds are 2,2-bis-(4-hydroxyphenyl)-propane(bisphenol A), 2,4-bis-(4-hydroxyphenyl)-2-methyl-butane, 1,1-bis-(4-hydroxyphenyl)-cyclohexane, α,α-bis-(4-hydroxyphenyl)-p-diisopropyl-benzene, 2,2-bis-(3-chloro-4-hydroxyphenyl)-propane, hydroxybenzophenone and 4,4'-sulfonyl diphenol; the most preferred one is 2,2-bis-(4-hydroxyphenyl)-propane(bisphenol A).

The polycarbonates of the invention may entail in their structure, units derived from one or more of the suitable bisphenols.

The preparation of polycarbonate resins may be carried out in accordance with any of the processes known in the art, for example, by the interfacial polycondensation process, polycondensation in a homogeneous phase or by transesterification.

The suitable processes and the associated reactants, catalysts, solvents and conditions are known in the art and have been described, inter alia, in German Pat. Nos. 1,046,311 and 962,274 and in U.S. Pat. Nos. 3,248,414; 3,153,008; 3,215,668; 3,187,065; 3,028,365; 2,999,846; 2,999,835; 2,964,974; 2,970,137; 3,912,638 and 1,991,273.

In the preparation of the polycarbonate resins of the invention monofunctional reactants such as monophenols may be used in order to limit their respective molecular weights. Branching agents may also be employed. Branching may be obtained by the incorporation of small amounts, preferably of between about 0.05 and 2.0 mol % (relative to diphenols employed), of trifunctional or more than trifunctional compounds, especially compounds having three or more phenyl (aromatic) hydroxyl groups. Polycarbonates of this type are described, for example, in German Offenlegungsschriften (German Published Specifications) Nos. 1,570,533; 1,595,762; 2,116,974 and 2,113,347; British Specification No. 1,079,821 and U.S. Pat. No. 3,544,514 (incorporated herein by reference).

Some examples of compounds with three or more than three phenyl hydroxyl groups which can be used are phloroglucinol, 4,6-dimethyl-2,4,6-tri-(4-hydroxyphenyl)-heptane, 2,4,6-trimethyl-2,4,6-tri-(4-hydroxyphenyl)-heptane, 1,4,5-tri-(4-hydroxyphenyl)-benzene, 1,1,1-tri-(4-hydroxyphenyl)-ethane, tri-(4-hydroxyphenyl)-phenylmethane, 2,2-bis[4,4-bis-(4-hydroxyphenyl)-cyclohexyl]-propane, 2,4-bis-(4-hydroxyphenylisopropyl)-phenol, 2,6-bis-(2-hydroxy-5'-methyl-benzyl)-4-methylphenol, 2-(4-hydroxyphenyl)-2-(2,4-dihydroxyphenyl)-propane, hexa(4-(4-hydroxyphenylisopropyl)-phenyl)-orthoterephthalic acid ester, tetra-(4-hydroxyphenyl)-methane, tetra-(4-(4-hydroxyphenylisopropyl)-phenoxy)-methane and 1,4-bis-((4',4''-dihydroxy-triphenyl)-methyl)-benzene. Some of the other trifunctional compounds are 2,4-dihydroxy-benzoic acid, trimesic acid, cyanuric chloride and 3,3-bis-(4-hydroxyphenyl)-2-oxo-2,3-dihydroindole.

Among the resins suitable in the practice of the invention are included phenolphthalein-based polycarbonate, copolycarbonates and terpolycarbonates such as are described in U.S. Pat. Nos. 3,036,036 and 4,210,741, both incorporated by reference herein.

The poly(alkylene)terephthalates suitable in the context of the present invention are thermoplastic polyesters which are normally crystalline polycondensation products of a difunctional organic alcohol or a reactive derivative thereof and a difunctional organic acid or a reactive derivative thereof. The alcohol may be aliphatic or mixed aliphatic-aromatic and the acid may be aromatic or mixed aliphatic-aromatic and in any case the organic groups may be straight-chained or branched, cyclic or polycyclic and may be unsubstituted or contain substituents such as alkyl, halogen, carboxyl, nitro, cyano, amido, imido or like radicals. Typical of the polyesters suitable in the practice of the invention are poly(alkylene)terephthalates or mixed terephthalates and isophthalates, wherein alkylene groups contain from 2 to 10, preferably from 2 to 6, carbon atoms. The most preferred are polyethylene terephthalate resins which are available commercially under such trade names as Tenite 6685 or Tenite 7741, both by Eastman Kodak Corporation, or which may be prepared by known techniques such as by the alcoholysis of esters of terephthalic acid with a glycol and subsequent polymerization and similar processes which are more fully described in U.S. Pat. Nos. 2,465,319, 3,047,539 and 3,516,957, all incorporated herein by reference.

The thermoplastic polyesters of the invention are further characterized in terms of their intrinsic viscosity—as measured in o-chlorophenol, a 60/40 phenol tetrachloroethane mixture or a similar solvent at 25°–30° C. The intrinsic viscosity may be at least 0.2 and preferably from about 0.4 to about 1.5 dl/g while the especially preferred resins will have a range of intrinsic viscosity of from 0.5 to 1.3 dl/g.

The flame retarding agent of the invention is incorporated in the thermoplastic resins in an amount sufficient to bring about an improvement in the flame retardance of these resins, preferably the amount thus incorporated is between about 0.01 and about 1.0 percent, more preferably between about 0.1 and about 0.75 percent, said percent being relative to the total weight of said resin and said flame retarding agent.

In a preferred embodiment of the invention, the compositions further contain small amounts of sulfonic or carboxylic acid salt. Specifically, the sulfonic or carboxylic acid salt is present in an amount of about 0.01 to about 3 percent, most preferably 0.05 to about 1 percent relative to the weight of the thermoplastic resin. Suitable sulfonic acid salts have been disclosed in U.S. Pat. No. 3,775,367 and in U.S. Pat. No. 4,391,935, both incorporated herein by reference.

The preferred sulfonic acid salts are sodium or potassium perfluorobutane sulfonates.

In embodiments entailing a branched polycarbonate resin, a rating of UL-94 V-0 for 1/16″ specimens is achieved with the addition of at least about 0.5 percent by weight of sulfonate salt.

Examples of suitable carboxylic acid salts in the sense of the invention are the alkali metal salts, especially the sodium salts and potassium salts, of aliphatic, aromatic or aliphatic-aromatic monobasic or dibasic, optionally halogenated, carboxylic acids with 1 to 24 carbon atoms, such as those of formic acid, acetic acid, propionic acid, butyric acid, isobutyric acid, valeric acid, caproic acid, oenanthic acid, caprylic acid, pelargnoic acid, capric acid, lauric acid, stearic acid, behenic acid, 5-ethyl-dioxan-1,3-yl-5-carboxylic acid, 3-(3,5-di-tert.-butyl-4-hydroxyphenyl)propionic acid, oleic acid, oxalic acid, malonic acid, succinic acid, glutaric acid, adipic acid, pimelic acid, sebacic acid, benzoic acid and its p-alkylated derivatives with 1 to 8 carbon atoms in the alkyl radical, salicyclic acid, terephthalic acid, isophthalic acid, phthalic acid monobenzyl ester, diglycolic acid monodecyl ester, adipic acid monobutyl ester and 3-chlorobenzoic acid.

An additional preferred embodiment entails admixing with the compositions of the invention an alkali metal salt of an inorganic acid. Lithium, sodium and potassium salts are preferred. Suitable inorganic acids include any compound which does not contain a carbon atom and meets the traditional tests of acidity. Among the suitable acids are the mineral acids and other Lewis acids which do not contain carbon atoms. Preferred acids are those that form salts with alkali metals which have pH values of about 7 or less.

The most preferred salts are the inorganic alkali metal complex fluoro anion salts, this terminology being derived from the discussion of fluorine compounds contained in the text Advanced Inorganic Chemistry by F. A. Cotton and G. Wilkinson, Interscience Publishers, 1962, at pages 290–294, these pages being incorporated herein by reference. Suitable inorganic alkali metal complex fluoro anion salts include $KBF_4$, $K_3AlF_6$, $KAlF_4$, $K_2SiF_6$, $Na_3AlF_6$, $KPF_6$, $NaSbF_6$, $Na_3FeF_6$, $NaPF_6$, $Na_2SiF_6$, $Na_2TiF_6$, $NaBF_4$, $K_2TaF_7$, $K_2NbF_7$, $KSbF_6$, $K_2NiF_6$, $K_2TiF_6$, $LiBF_4$, $LiPF_6$ and $LiBeF_4$.

$KBF_4$, $K_3AlF_6$, $KAlF_4$, $K_2SiF_6$ and $Na_3AlF_6$ are the preferred inorganic alkali metal complex fluoro anion salts, and $Na_3AlF_6$ is the most preferred inorganic alkali metal complex fluoro anion salt.

The inorganic alkali metal complex fluoro anion salts may be used in any effective amount up to about 2 wt. % based on the weight of the polymer resin. It is preferred to use no less than about 0.01 wt. % and more preferably no less than about 0.1 wt. %. It is also preferred to use no more than about 1 wt. % and more preferably about 0.5 wt. %. Amounts higher than 2 wt. % of salt will not decrease its effect upon flame retardance but may cause a degree of degradation in the other properties of the resin greater than is justified by the improvement in flame retardancy.

Naturally, any particular salt which is known to have characteristics likely to make it unacceptable for use in polymer resins should be avoided. For instance, salts which decompose at the processing temperatures of the resins into which they are incorporated should be avoided.

The thermoplastic molding compositions of the invention may contain further flame retarding additives and drip suppressants, for instance PTFE (i.e., polytetrafluoroethylene). Other additives such as are commonly used in thermoplastic molding compositions, including reinforcing agents, fillers, pigments, dyes, UV stabilizers, hydrolytic stabilizers, mold release agents and plasticizers may be incorporated as well.

The invention is further illustrated, but is not intended to be limited by the following examples in which all parts and percentages are by weight unless otherwise specified.

EXAMPLES

Examples 1 and 2 demonstrate the preparation of the novel compounds of the invention.

EXAMPLE 1

N-(tetrabromophthalimido)propyltris(ethoxy)silane, conforming to

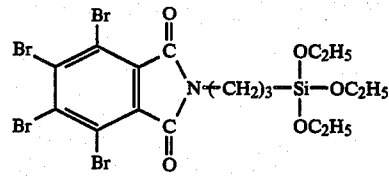

was thus prepared: 46.4 g (0.1 mole) of tetrabromophthalic anhydride was added to 185.6 g of toluene. To this solution was added 2.32 g of glacial acetic acid (5 wt. % based on the weight of anhydride). After heating the mixture to 100° C., a solution of 22.1 g (0.1 mole) of aminopropyltris(ethoxy)silane in 66.3 g of methanol was added dropwise. During the addition of aminopropyltris(ethoxy)silane, toluene, methanol as well as water from the reaction were simultaneously distilled. The mixture was heated for an additional two hours and the product was filtered and dried at 80° C. under vacuum. 53.5 g of product was obtained, characterized in that its melting point was 137° C. and in that its nitrogen content was 2.33% (compare to 2.1% theoretical content).

EXAMPLE 2

Further demonstrating a synthesis of the novel compound is the preparation of N-(tetrachlorophthalimido)α,α,α-tris(ethoxy)silylpropane which is described below:

The procedure described above was followed except that tetrachlorophthalic anhydride was used. The product was characterized by its nitrogen content of 3.23% (compare to the theoretical 2.86%).

EXAMPLES 3–5

Conventional procedures commonly employed in preparing polycarbonate molding compositions were employed in preparing the following embodiments of the invention. The amounts of the components are noted in parts per hundred weight of resin.

3. A transparent molding composition containing a branched homopolycarbonate based on bisphenol-A, having a melt flow rate (per ASTM D-1238) of about 2.4 g/10 min. (Merlon HMS 3119 from Mobay Chemical Corporation), 0.5 phr of N-(tetrabromophthalimido)propyltris(ethoxy)silane, and 0.1 phr of potassium perfluorobutane sulfonate, was molded and its properties determined. The (notched) Izod impact strength, ⅛″ specimens was about 14.1 ft.lb./in. and the flammability ratings in accordance with UL-94 was V-0 for both ⅛" and 1/16" specimens with a corresponding average burn time of 1.7 and 4.2 seconds.

4. An opaque molding composition containing Merlon M-40 which is a linear homopolycarbonate based on bisphenol-A (melt flow rate of about 6.0–11.9 gm/10 min.), 0.15 phr of N-(tetrabromophthalimido)propyl-tris(ethoxy)silane, 0.15 phr of PTFE and 0.25 phr of cryolite, i.e. Na$_3$AlF$_6$, was prepared and its properties determined. The notched impact (Izod) of ⅛" specimens was about 16 ft.lb./in. and the flammability rating per UL-94 was V-O for both ⅛" and 1/16" specimens; the average burn time (seconds) was 1.3 and 2.8 seconds, respectively.

5. A molding composition based on the same resin as in B above was prepared containing 0.15 phr of the silane and 0.15 phr of the PTFE as noted for Example B, and 0.25 phr of potassium perfluorobutane sulfonate. The impact strength (notched Izod, ⅛") was about 15 ft.lb./in. and the UL-94 rating was V-0 for ⅛" and 1/16" specimens with an average burn time of 1.0 and 4.5 seconds, respectively.

The UL-94 flammability rating of 1/16" specimens of the compositions of the invention are compared favorably with prior art compositions. For instance, a composition based on Merlon HMS-3119 containing 0.1 phr of potassium perfluorobutane sulfonate rated V-1. A further addition of 1.0 phr of oligomeric tetrabromo BPA polycarbonate did not improve the rating.

Also, HMS-3119 based composition containing 0.15 phr of PTFE failed UL-94 V-2 and a composition containing the same base resin and 0.5 phr of oligomeric tetrabromo BPA-polycarbonate rated V-2 in accordance with the same test.

Further evidence of the advantage offered by the present invention is seen in that a composition based on Merlon M-40 and similar in all respects to Example 4 above except for the deletion of the silane therefrom was determined to have a UL-94 rating of V-1 at 1/16" specimens, with an average burn time of greater than 5 seconds.

The invention has been described with particular reference to specific materials yet such should not be viewed as in any way limiting the scope of the invention which is set forth in the following claims.

What is claimed is:
1. The compound

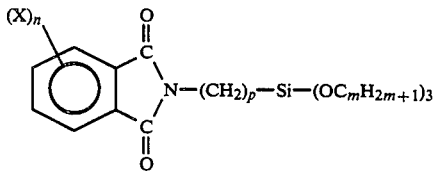

wherein X is a halogen atom, n is 1–4, p is 1–9 and m is 1–5.

2. The compound

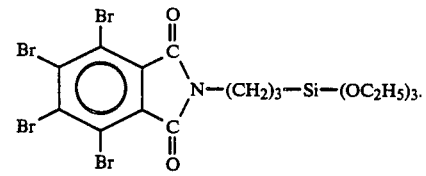

3. The compound

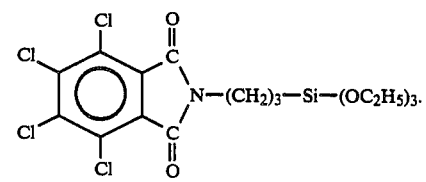

4. A thermoplastic molding composition comprising (i) a thermoplastic resin selected from the group consisting of aromatic polycarbonates and thermoplastic polyesters and (ii) a flame retarding amount of the compound of claim 1.

5. The composition of claim 4 wherein said resin is a homopolycarbonate based on bisphenol-A.

6. The composition of claim 5 wherein said resin is branched.

7. The composition of claim 4 wherein said amount is between 0.01 and about 1.0 percent relative to the weight of said resin.

8. The composition of claim 4 further comprising about 0.01 to about 3 percent relative to the weight of the resin of a sulfonic or a carboxylic acid salt.

9. The composition of claim 8 wherein said salt is potassium perfluorobutane sulfonate.

10. The composition of claim 4 further comprising sufficient amounts of PTFE and of an inorganic alkali metal complex fluoro anion salt to render the composition V-0 for 1/16" specimens in accordance with UL-94.

11. The composition of claim 10 wherein said inorganic alkali metal complex fluoro anion salt is cryolite.

* * * * *